(12) United States Patent
Takai et al.

(10) Patent No.: US 6,479,711 B1
(45) Date of Patent: Nov. 12, 2002

(54) PROCESS FOR PRODUCING AROMATIC HYDROXY COMPOUND

(75) Inventors: Toshihiro Takai; Kazuaki Matsui, both of Yamaguchi (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/559,069

(22) Filed: Apr. 28, 2000

(30) Foreign Application Priority Data

Apr. 28, 1999 (JP) .......................................... 11-121647

(51) Int. Cl.[7] .............................................. C07C 37/06
(52) U.S. Cl. ....................... 568/771; 568/741; 568/753; 568/629; 568/803
(58) Field of Search ................................ 568/741, 771, 568/803, 753, 629

(56) References Cited

U.S. PATENT DOCUMENTS

| | | |
|---|---|---|
| 4,410,501 A | 10/1983 | Taramasso et al. |
| 5,245,086 A | 9/1993 | Costantini et al. |
| 5,254,746 A | 10/1993 | Costantini et al. |
| 5,426,244 A | 6/1995 | Sugai et al. ................. 568/771 |

FOREIGN PATENT DOCUMENTS

| | | |
|---|---|---|
| EP | 0230949 A2 | 8/1987 |
| EP | 0568336 A2 | 11/1993 |
| EP | 0638362 A1 | 2/1995 |
| EP | 0894783 A1 | 2/1999 |
| FR | 2730722 | 8/1996 |
| JP | 2298350 | 12/1990 |
| JP | 466546 | 3/1992 |
| JP | 07002714 A | 6/1995 |

OTHER PUBLICATIONS

Nature, 165, 400–403 (1950).
Vesely et al., J. Org. Chem., vol. 35, No. 12 (1970), 4028–4033.
Vankelecom et al., J. Chem. Soc., Chem Commn., (1997) 137–138.

*Primary Examiner*—Sreeni Padmanabhan
(74) *Attorney, Agent, or Firm*—Birch, Stewart, Kolasch & Birch, LLP

(57) ABSTRACT

A process for producing an aromatic hydroxy compound having hydroxyl group at the para-position with respect to a hydroxy or an alkoxy substituent group present in the aromatic ring at a high yield and at a high selectivity, using a novel and useful hydroxylation catalyst which can afford to introduce hydroxyl group directly into aromatic ring at the para-position with respect to a hydroxy or an alkoxy substituent group, by reacting at least one compound selected from the group consisting of phenols, alkoxybenzenes and derivatives of them with hydrogen peroxide in the presence of the catalyst, wherein the hydroxylation catalyst is constituted of an oleophilized crystalline titanosilicate.

11 Claims, No Drawings

PROCESS FOR PRODUCING AROMATIC HYDROXY COMPOUND

FIELD OF THE INVENTION

The present invention relates to a catalyst for hydroxylating an aromatic compound and to a process for producing an aromatic hydroxy compound using such catalyst, in particular, by hydroxylating a phenol by hydrogen peroxide to obtain the contemplated aromatic hydroxy compound. The aromatic hydroxy compound, such as hydroquinone or catechol, to be produced by the production process according to the present invention is useful as an intermediate or a starting material for synthesizing various organic compounds and has found its application to fields of, such as reducing agent, rubber additives, dyestuffs, medicaments, agricultural chemicals, polymerization inhibitor and antioxidants.

BACKGROUND OF THE INVENTION

There had, from of old, been known for hydroxylating a phenol using hydrogen peroxide a method in which the reaction is performed in the presence of divalent iron ion {Nature, 165, 401 (1950)}, a method in which hydrofluoric acid is employed {J. Org. Chem., 35, 4028 (1970)} and so on. It was also reported that a technique using pyrophosphoric acid in combination with perchloric acid or an alkaline earth metal salt thereof is industrially useful {Japanese Patent Kokai Hei 3-240743 A (corresponding to U.S. Pat. No. 5,245,086)}.

However, these prior art methods reveal problems in that laborious and bothersome works are required for isolation of the contemplated compound by removing the catalyst from the reaction product, since the catalyst is dissolved in the reaction liquor homogeneously; that a precious material is required for the apparatus for the reaction due to the use of a highly corrosive acid; and that neutralization with a base is required for disposal of the spent catalyst acid.

Afterwards, techniques were proposed, in which a catalyst of heterogeneous system for easy removal from the reaction mixture, for example, crystalline titanosilicate or the like, is used {Japanese Patent Kokai Hei 1-149744 A (corresponding to EP No. 314582 A and to U.S. Pat. No. 5,254,746), Japanese Patent Kokai Hei 2-298350 A and Japanese Patent Kokai hei 4-66546 A}. Among these prior art techniques, a method using a crystalline titanosilicate of MFI structure is industrially advantageous, since the removal of the catalyst from the reaction product can be effected simply by a physical means. However, there remains a problem in that all these prior art techniques can attain a lower selectivity, since hydroquinone and catechol are formed by the hydroxylation reaction in nearly equal proportion.

In order to obviate these problems, there was proposed a technique in which a phenol is subjected to a hydroxylation with hydrogen peroxide in the presence of a cyclic ether, such as dioxane or the like, and of a crystalline titanosilicate catalyst {Japanese Patent Kokai Hei 5-170684 A (corresponding to U.S. Pat. No. 5,426,244) and Japanese Patent Kokai Hei 6-263670 A (corresponding to U.S. Pat. No. 5,426,244) and Japanese Patent Kokai Hei 7-2714 A}. In these Patent Gazettes, it is noted that the selectivity of hydroquinone becomes increased by the addition of a cyclic ether. In this prior technique, however, the hydroquinone/catechol ratio amounts to only about 7/1 and, therefore, a more pronounced suppression of by-production of catechol is desirable.

SUMMARY OF THE INVENTION

The first object of the present invention is to provide a novel and useful catalyst for hydroxylation of an aromatic compound having a hydroxy or an alkoxy substitutent group, which catalyst can afford to introduce a hydroxyl group directly into the aromatic ring at the para-position with respect to the hydroxy or the alkoxy substituent group at a high selectivity.

The second object of the present invention is to propose a process for producing an aromatic hydroxy compound, in which a hydroxyl group is introduced in the aromatic ring at the para-position with respect to a hydroxy or an alkoxy substitutent group on the aromatic ring, which process can afford to produce the aromatic hydroxy compound in a simple manner at a high yield and at a high selectivity.

Thus, the present invention consists in the catalyst for hydroxylation and the process for producing an aromatic hydroxy compound as given below:

(1) A catalyst for hydroxylation of an aromatic compound comprising an oleophilized crystalline titanosilicate.
(2) The catalyst as defined in the above (1), wherein the oleophilization is effected with an organosiloxane.
(3) The catalyst as defined in the above (2), wherein the organosiloxane is a dialkylsiloxane oligomer.
(4) The catalyst as defined in at least one of the above (1) to (3), wherein the crystalline titanosilicate has a structure of MFI.
(5) A process for producing an aromatic hydroxy compound, comprising reacting at least one compound selected from the group consisting of phenols, alkoxybenzenes and derivatives of them with hydrogen peroxide in the presence of a catalyst as defined in any one of the above (1) to (4).
(6) A process for producing an aromatic hydroxy compound, comprising reacting at least one compound selected from the group consisting of phenols, alkoxybenzenes and derivatives thereof with hydrogen peroxide in the presence of a compound having ether linkage and of a catalyst as defined in any one of the above (1) to (4).

DETAILED DESCRIPTION OF THE INVENTION

For the crystalline titanosilicate to be oleophilized, those represented by the structural formula $(SiO_2)_x \cdot (TiO_2)_{1-x}$ may be employed without any restriction. For the ratio x/(1−x), namely, the Si/Ti atomic ratio, of the crystalline titanosilicate, there is no special restriction, while usually preference is given to those in the range from 1 to 10,000, preferably from 5 to 1,000, especially preferably from 10 to 500. For the crystalline titanosilicate, those of MFI type having MFI structure are preferred.

The crystalline titanosilicate can be prepared by known techniques. It may be produced, for example, by formulating first a reaction mixture composed of a silicon source, a titanium source, nitrogen source and water and subjecting the mixture then to a hydrothermal synthesis. As the silicon source, there may be employed, for example, alkoxides of silicon and colloidal silica. As the titanium source, there may be exemplified alkoxides of titanium, titanium halides, titanic acid and titanium sulfide. As the nitrogen source, there may be enumerated nitrogen-containing compounds, for example, quaternary ammonium salts, such as salts of tetrapropyl ammonium and tetrabutyl ammonium.

As a concrete technique for producing the crystalline titanosilicate, the following method may be exemplified. The mixture of the silicon source, the titanium source, the nitrogen source and water as given above is agitated while adjusting the pH thereof at an adequate value, whereby a gel-formed precipitate is formed. This precipitate is then subjected to a hydrothermal reaction while heating at a temperature of 100–250° C. for 1–100 hours to obtain a solid product. This solid product is washed with deionized water and dried, whereupon it is calcined at a temperature of 400–600° C. in air, whereby the crystalline titanosilicate is obtained. In such a production method, a crystalline titanosilicate of MFI structure can easily be obtained, when a tetrapropyl ammonium salt is employed as the nitrogen source.

Processes were disclosed for producing crystalline titanosilicates in, for example, Japanese Patent Kokai Sho 56-96720 A (corresponding to U.S. Pat. No. 4,410,501) and Japanese Patent Kokai Hei 4-66546 A and the crystalline titanosilicates produced by these processes can also be employed. As the crystalline titanosilicate, commercial products may also be used. Also, for the MFI type crystalline titanosilicate, commercial products can be used.

For oleophilizing the crystalline titanosilicate, there may be employed, for example, a method in which the crystalline titanosilicate is treated with a compound having oleophilic group(s) to cause the crystalline titanosilicate to carry the oleophilic group-containing compound.

As the oleophilic group, there may be exemplified aliphatic hydrocarbyls such as alkyls etc., aromatic hydrocarbyls such as phenyl and the like, halogenated hydrocarbyls such as halogenated alkyls etc. including fluorocarbyls such as trifluoromethyl and the like.

For the oleophilic group-containing compound, those having the oleophilic group(s) given above can be employed without any restriction. It is permissible that the oleophilic group-containing compound contains one or more oleophilic groups. As the oleophilic group-containing compound, organosiloxanes having the oleophilic group(s) given above are preferred, wherein preference is given in particular to an organosiloxane having Si—H bonds in a part of the molecule together with the oleophilic group(s). Siloxane is a compound having Si—O bond in the molecule. For such organosiloxanes, there may be enumerated, for example, linear dialkylsiloxane oligomers having Si—H bond(s) in a part of the molecule, exemplified concretely by dimethylsiloxane oligomers. For the dialkylsiloxane oligomer, commercial products may be employed. There may be exemplified KF-99 (trademark) of Shin-Etsu Chemical Co., Ltd. and RTV-615 (trademark) of General Electric Co. The oleophilic group-containing compound may be employed solely or in a combination of two or more of such compounds.

The proportion of the oleophilic group-containing compound carried on the crystalline titanosilicate may favorably be in the range from 1 to 30 parts by weight, preferably from 2 to 20 parts by weight, per 100 parts by weight of the original crystalline titanosilicate. If the proportion is in the range of 1–30 parts by weight, such advantageous features will be attained, that the catalytic function will easily be revealed, that the catalytic activity will scarcely be reduced and that the rate of disappearance of hydrogen peroxide may difficultly be decreased.

A practical way for rendering the crystalline titanosilicate oleophilic by causing the crystalline titanosilicate to carry one or more organosiloxanes includes a method comprising bringing the organosiloxane into contact with the crystalline titanosilicate, followed by a procedure for effecting bridging of them through an oxygen atom to combine together to form a higher molecular weight product, whereby the organosiloxane is fixed onto the crystalline titanosilicate. Here, the treatment by contacting them may be realized by dissolving the organosiloxane in a solvent and adding the crystalline titanosilicate to the resulting solution with agitation. The bridging and fixing may be effected by, for example, heating the contacting-treated crystalline titanosilicate in air to bake it.

Now, the practical manner of subjecting the crystalline titanosilicate to the oleophilizing treatment by the organosiloxane is described concretely with reference to an example of using a dialkylsiloxane oligomer. First, the dialkylsiloxane oligomer is dissolved in n-hexane at room temperature. To the so-obtained solution, there is added the crystalline titanosilicate and the mixture is agitated in the atmospheric air at room temperature for a duration of 0.1 to 48 hours. The mixing proportion of them may preferably be in the range from 1 to 30 parts by weight of the dialkylsiloxane oligomer per 100 parts by weight of the crystalline titanosilicate. The resulting mixture is then freed from n-hexane under a reduced pressure and the residue is subjected to vacuum drying at a temperature of 20–150° C. The resulting mass is then baked in air at a temperature of 100–300° C. for 1–24 hours to cause the dialkylsiloxane oligomer to be bound to the crystalline titanosilicate. Hereby a crystalline titanosilicate oleophilized by the dialkylsiloxane oligomer is obtained. It is permissible to incorporate other organic siloxane compound instead of the dialkylsiloxane oligomer or to employ other solvent in the place of n-hexane.

Methods have been disclosed for olephilizing a crystalline titanosilicate by an organosiloxane, for example, in J. Chem. Soc., Chem. Commn., (1997) 137, which are of course applicable to the oleophilization of the crystalline titanosilicate according to the present invention.

The catalyst according to the present invention has a catalytic function to hydroxylate directly the aromatic ring of an aromatic compound and is thus a nuclear-hydroxylating catalyst. By the catalyst according to the present invention, a reaction product can be produced, in which, usually, one hydroxyl group is introduced into the aromatic ring of the starting aromatic compound or, in particular, a hydroxyl group is introduced into the aromatic ring of a starting aromatic compound at the para-position with respect to the hydroxy or the alkoxy substituent group present in the starting aromatic compound. The catalyst according to the present invention is a heterogeneous system catalyst and can be separated from the reaction system easily by, for example, filtration or the like.

While there is no special restriction for the aromatic compound to be hydroxylated (in the following, denoted sometimes as "the starting compound") according to the present invention so long as it has an aromatic ring, preference is given to those in which one or more hydroxy or alkoxy substituent groups are bound to the aromatic ring, preferably of monocyclic ones in which a single such substituent group is bound to the aromatic ring, for example, phenol, alkoxy benzenes and derivatives, such as alkyl derivatives, of them. Here, the resulting product may be a divalent phenol, an alkoxyphenol or a derivative thereof, such as an alkyl derivative of them.

Concrete examples of the starting compounds, such as phenols and derivatives thereof include phenol, cresol, xylenol, hydroquinone and resorcin. Concrete examples of alkoxybenzene and derivatives thereof include anisole, diphenyl ether, isopropyl phenyl ether and so on.

Concrete examples of the reaction product include hydroquinone, catechol, 4-methoxyphenol, 2-methoxyphenol, 2-methylhydroquinone, 3-methylcatechol, 4-methylcatechol, 3-methylhydroquinone, 1,4-dimethylhydroquinone, 1,4-dimethylcatechol, 3,5-dimethylcatechol, 2,3-dimethylhydroquinone, 2,3-dimethylcatechol, 1,2,4-benzenetriol, 4,4'-dihydroxyphenyl ether and isopropyl 4-hydroxyphenyl ether.

When a phenol or an alkoxybenzene or a derivative thereof is employed for the starting aromatic compound, it is able to introduce a hydroxyl group directly into the aromatic ring at the para-position with respect to the hydroxy or the alkoxy substituent group at a high selectivity and at a high yield.

As the starting compound, phenol is at the most preferred, wherein hydroquinone can be obtained as the reaction product at a high selectivity and at a high yield, with suppressed by-production of catechol.

By the production process according to the present invention, an aromatic hydroxy compound in which a hydroxyl group is introduced into the aromatic ring at the para-position with respect to the hydroxy or the alkoxy substituent group present in the starting aromatic compound can be produced in a simple manner at a high selectivity and at a high yield. As the starting compound, phenol is preferred, wherein hydroquinone can be produced at high yield at a high selectivity with suppressed by-production of catechol.

The amount of the catalyst to be incorporated may favorably be in the range from 0.5 to 50 parts by weight, preferably from 2 to 30 parts by weight, per 100 parts by weight of the starting compound. When the catalyst is employed in an amount within the range from 0.5 to 50 parts by weight per 100 parts by weight of the starting compound, the period of time till the completion of the reaction at which hydrogen peroxide added disappears will become decreased and a high productivity will be attained.

The amount of hydrogen peroxide to be used may favorably be in the range from 0.02 to 0.5 mole, preferably from 0.05 to 0.3 mole, with respect to one mole of the starting compound. Hydrogen peroxide is incorporated usually in a form of an aqueous hydrogen peroxide solution, wherein no special restriction is placed on the concentration thereof and it is permissible to use a conventional aqueous hydrogen peroxide solution of about 30% by weight or to use a high concentration aqueous hydrogen peroxide solution under dilution in the reaction system with an inert medium.

It is favorable that the reaction temperature lies in the range from 50 to 130° C., preferably from 60 to 100° C. When the reaction temperature is within the range of 50–130° C., the period of time till the completion of the reaction at which hydrogen peroxide added disappears will become decreased and a high productivity will be attained. There is also a tendency to a higher yield of the reaction product. The reaction duration may favorably be in the range from 0.2 to 30 hours, preferably from 0.5 to 10 hours. The a reaction pressure will not specifically be limited.

The reaction can be effected using the water of the aqueous hydrogen peroxide solution as such for the reaction medium or under addition of an inert reaction medium to the reaction system. As the reaction medium, there may be employed, for example, acetonitrile, ethanol, methanol and water. When an intrinsic reaction medium is used, the amount thereof to be used may, in general, favorably be in the range of 10–200 parts by weight, preferably 20–150 parts by weight, per 100 parts by weight of the starting compound, though there is no special restriction.

In the production process according to the present invention, the reaction may favorably be effected in the co-existence of a compound having ether linkage. When the reaction is performed in the presence of a compound having ether linkage, the introduction of hydroxyl group into the aromatic ring at the para-position with respect to the hydroxy or the alkoxy substitutent group present in the starting compound can be realized at a more higher selectivity.

As the compound having ether linkage, there may be enumerated, for example, cyclic ethers, such as 1,4-dioxane, 1,3-dioxane, 1,3-dioxolane and tetrahydrofuran; and linear polyethers having about 4–10 carbon atoms, such as ethylene glycol dimethyl ether, ethylene glycol diethyl ether, propylene glycol dimethyl ether and diethylene glycol dimethyl ether.

The amount of the compound having ether linkage to be incorporated may favorably be in the range of 1–100 parts by weight, preferably 2–50 parts by weight, per 100 parts by weight of the starting aromatic compound. When such ether compound is incorporated in the reaction system in an amount in the range of 1–100 parts by weight per 100 parts by weight of the starting compound, the above-mentioned effect of co-existence of such ether compound is acceptably high with accompaniment of an advantage of reduction of the work for recovering the ether compound.

The reaction can be effected either in a batchwise operation or in a continuous operation. For a continuous operation, the reaction may be realized either in a suspension in a homogeneous mixing tank or in a once-through solid bed reactor in a plug flow. It is permitted to recycle the recovered unreacted starting compound to use it again for the reaction.

The aromatic hydroxy compound, such as hydroquinone and catechol, obtained in this manner is useful as an intermediate or a raw material for various organic syntheses and can be utilized in the fields of, such as reducing agent, rubber additives, dyestuffs, medicaments, agricultural chemicals, polymerization inhibitor and antioxidant.

As described above, the present invention provides a novel and useful hydroxylation catalyst which can afford to introduce hydroxyl group into an aromatic ring having a hydroxy or alkoxy substituent group directly at the para-position of such substituent group at a high selectivity. By reacting at least one aromatic compound selected from the group consisting of phenols, alkoxybenzenes and derivatives of them with hydrogen peroxide using the above catalyst, an aromatic hydroxy compound having a hydroxyl group introduced therein at the para-position with respect to the hydroxy or alkoxy substituent group present in the starting aromatic compound can be produced in a simple manner at a high selectivity and at a high yield. By concurrent use of a compound having ether linkage, the selectivity can further be increased.

THE BEST MODE FOR EMBODYING THE INVENTION

Below, the present invention will further be described by way of Examples.

EXAMPLE 1

In a 100 ml eggplant type glass flask, there were charged 2 grams of a crystalline titanosilicate TS-1 (a product of the firm N. E. Chemcat, with Si/Ti atomic ratio of 25), 0.05 gram of an organosiloxane (a dimethylsiloxane oligomer with a trademark of KF-99 of Shin-Etsu Chemical Co., Ltd.) and 20 ml of n-hexane and the mixture was agitated in the atmospheric air at room temperature for 1 hour. Then, the solvent was distilled off under a reduced pressure and the residue was dried under vacuum at a temperature of 100° C. for 1 hour, whereupon the dried mass was baked in the atmospheric air at 200° C. for 1 hour, whereby a dimethylsiloxane oligomer-treated product of TS-1 was obtained. The amount of the dimethylsiloxane oligomer in the so-obtained catalyst was found to be 2.5 parts by weight per 100 parts by weight of the starting crystalline titanosilicate.

EXAMPLE 2

In a 100 ml eggplant type glass flask, there were charged 2 grams of TS-1 mentioned above, 0.10 gram of KF-99 mentioned above and 20 ml of n-hexane and the mixture was agitated in the atmospheric air at room temperature for 1 hour. Then, the solvent was distilled off under a reduced pressure and the residue was dried under vacuum at a temperature of 100° C. for 1 hour, whereupon the dried mass was baked in the atmospheric air at 200° C. for 1 hour, whereby a dimethylsiloxane oligomer-treated product of TS-1 was obtained. The amount of the dimethylsiloxane oligomer in the so-obtained catalyst was found to be 5 parts by weight per 100 parts by weight of the starting crystalline titanosilicate.

EXAMPLE 3

In a 25 ml double necked eggplant type flask equipped with a Dimroth condenser, there were charged 6.5 grams of phenol of special grade chemical, 3.0 grams of distilled water, 2.0 grams of 1,4-dioxane and 0.65 gram of the dimethylsiloxane oligomer-treated TS-1 obtained in Example 1 and the mixture was agitated by magnetic stirrer on an oil bath of 85° C. under a nitrogen atmosphere. Thereto was added 0.5 ml of aqueous solution of hydrogen peroxide of 30wt. % concentration using a syringe and the heating agitation was further continued. In the course of continuing the heating agitation for further two hours, each 0.5 ml of the aqueous hydrogen peroxide solution was added to the reaction mixture at each occasion after 40 minutes and 80 minutes, respectively. After completion of the reaction, the reaction mixture was cooled to room temperature and was freed from the catalyst using a Kiriyama separating funnel while adding a small amount of 1,4-dioxane, whereby a red brown reaction mixture was obtained.

The amounts of phenol, hydroquinone and catechol in the reaction mixture were quantitatively analyzed by a gas chromatography. The conversion yield and the selectivity were calculated from the disappeared amount of the starting phenol used and from the formed amounts of hydroquinone and catechol, respectively. The conversion yield was found to be 19.0 mole % and the selectivities for hydroquinone and for catechol were found to be 67.1 mole % and 6.0 mole %, respectively.

EXAMPLE 4

The reaction was performed in the same manner as in Example 3, except that the catalyst obtained in Example 2 was employed instead of the catalyst obtained in Example 1. As a result, the conversion yield of phenol was found to be 19.8 mole % and the selectivities for hydroquinone and for catechol were found to be 66.3 mole % and 6.3 mole %, respectively.

COMPARATIVE EXAMPLE 1

The reaction was performed in the same manner as in Example 3, except that crystalline titanosilicate TS-1 was employed as such without being subjected to the surface treatment. As a result, the conversion yield of phenol was found to be 19.0 mole % and the selectivities for hydroquinone and for catechol were found to be 62.3 mole % and 6.7 mole %, respectively.

What is claimed is:

1. A process for producing an aromatic hydroxy compound, comprising reacting at least one compound selected from the group consisting of phenols, alkoxybenzenies and derivatives thereof with hydrogen peroxide in the presence of a catalysts said catalyst comprising an oleophilized crystalline titanosilicate.

2. A process for producing an aromatic hydroxy compound, comprising reacting at least one compound selected from the group consisting of phenols, alkoxybenzenes and derivatives thereof with hydrogen peroxide in the presence of a compound having ether linkage and of a catalyst, said catalyst comprising an oleophilized crystalline titanosilicate.

3. The process of claim 1 or 2, wherein said crystalline titanosilicate is produced by oleophilization with an organosiloxane.

4. The process of claim 3, wherein said organosiloxane is a dialkylsiloxane oligomer.

5. The process of claim 3, wherein said crystalline titanosilicate has a structure of MFI.

6. The process of claim 1 or 2, wherein said phenols, and derivatives thereof, are selected from the group consisting of phenol, cresol, xylenol and resorcin.

7. The process of claim 1 or 2, wherein said catalyst is in the amount of 0.5 to 50 parts by weight per 100 parts of said phenols, alkoxybeenzenes or derivatives thereof.

8. The process of claim 1 or 2, wherein said hydrogen peroxide is in the amount of 0.02 to 0.5 mole with respect to one mole of said phenols, alkoxybenzenes or derivatives thereof.

9. The process of claim 1 or 2, wherein said reaction is conducted at a temperature of 50° C. to 130° C.

10. The process of claim 2, wherein said compound having ether linkage is selected from the group consisting of 1,4-dioxane, 1,3-dioxane, 1,3-dioxolane, tetrahydrofuran, ethylene glycol dimethyl ether, ethylene glycol diethyl ether, propylene glycol dimethyl ether and diethylene glycol dimethyl ether.

11. The process of claim 4, wherein said crystalline titanosilicate has a structure of MFI.

* * * * *

UNITED STATES PATENT AND TRADEMARK OFFICE
CERTIFICATE OF CORRECTION

PATENT NO.   : 6,479,711 B1
DATED        : November 12, 2002
INVENTOR(S)  : Toshihiro Takai et al.

It is certified that error appears in the above-identified patent and that said Letters Patent is hereby corrected as shown below:

<u>Column 8,</u>
Lines 20-21, please change "alkoxybenzenies" to -- alkoxybenzenes --.
Line 22, please change "catalysts" to -- catalyst --.
Line 44, please change "alkoxybeenzenes" to -- alkoxybenzenes --.

Signed and Sealed this

Fifteenth Day of April, 2003

JAMES E. ROGAN
*Director of the United States Patent and Trademark Office*